United States Patent [19]

Bacehowski et al.

[11] Patent Number: 4,939,151
[45] Date of Patent: Jul. 3, 1990

[54] ADHERENT CELL CULTURE FLASK

[75] Inventors: David V. Bacehowski, Wildwood; Julian P. Breillatt, Jr., Mundelein; William Kolanko, Grayslake; Sidney T. Smith, Lake Forest, all of Ill.

[73] Assignee: Baxter International Inc., Deerfield, Ill.

[21] Appl. No.: 382,051

[22] Filed: Jul. 13, 1989

Related U.S. Application Data

[63] Continuation of Ser. No. 264,595, Oct. 31, 1988, abandoned.

[51] Int. Cl.$^5$ .............................................. C12M 3/00
[52] U.S. Cl. ................... 435/284; 435/287; 435/296; 383/35; 383/102; 206/484.1
[58] Field of Search ............... 435/287, 292, 294, 296, 435/284; 383/35, 41, 102; 206/484.1

[56] References Cited

U.S. PATENT DOCUMENTS

| | | |
|---|---|---|
| 3,419,654 | 12/1968 | Chiba et al. |
| 3,661,674 | 5/1972 | Higgs et al. |
| 3,885,081 | 5/1975 | Van Paesschen et al. |
| 3,912,843 | 10/1975 | Brazier |
| 3,960,997 | 6/1976 | Sorensen |
| 4,045,515 | 8/1977 | Isaka et al. |
| 4,085,244 | 4/1978 | Stillman |
| 4,112,989 | 9/1978 | Grode et al. |
| 4,156,709 | 5/1979 | Kondo et al. |
| 4,161,562 | 7/1979 | Yoshikawa et al. |
| 4,188,350 | 2/1980 | Vicik et al. |
| 4,226,822 | 10/1980 | Yoshikawa et al. |
| 4,261,473 | 4/1981 | Yamada et al. |
| 4,274,900 | 6/1981 | Mueller et al. |
| 4,294,935 | 10/1981 | Kodera et al. |
| 4,333,968 | 6/1982 | Nahmias |
| 4,362,844 | 12/1982 | Lemstra et al. |
| 4,421,235 | 12/1983 | Moriya ............................ 206/484.1 |
| 4,572,854 | 2/1986 | Dallmann et al. |
| 4,614,781 | 9/1986 | Hori et al. |
| 4,621,014 | 11/1986 | Lu |
| 4,654,240 | 3/1987 | Johnston |
| 4,680,208 | 7/1987 | Aoki et al. |
| 4,724,961 | 2/1988 | Shimoyamada et al. ......... 206/484.1 |
| 4,829,002 | 5/1989 | Pattillo et al. ...................... 435/287 |

FOREIGN PATENT DOCUMENTS

0148161 10/1985 European Pat. Off.
2800437 7/1978 Fed. Rep. of Germany ...... 435/287

OTHER PUBLICATIONS

Defensive Publication T904,013, Nov. 7, 1972.
McKeehan, Culture Surface, Cell Culture Subculturing, Serum Requirements, pp. 120-121 and 126, (date unknown).
Ratner et al., Biomaterial surfaces, Journal of Biomedical Materials Research: Applied Biomaterials, vol. 21 (1987) pp. 59-89.
P. B. van Wachem et al., The influence of protein adsorption on interactions of cultured human endothelial cells with polymers, Journal of Biomedical Materials Research, vol. 21 (1987) pp. 701-718.
Vogler et al., Short-term cell-attachment rates: A surface-sensitive test of cell-substrate compatibility, Journal of Biomedical Materials Research, vol. 21 (1987) pp. 1197-1211.

Primary Examiner—Carroll B. Dority
Attorney, Agent, or Firm—Bradford R. L. Price; Paul C. Flattery; Robert M. Barrett

[57] ABSTRACT

An adherent cell culture flask is provided. The flask includes a body constructed from a first side wall and a second side wall, each side wall having an interior surface and an exterior surface. The first and second side walls are sealed together to define a chamber. The first side wall is constructed from flexible film and includes on its interior surface a charged surface for facilitating the attachment of cells thereto. The second side wall is constructed from flexible film and includes a non-smooth interior surface for preventing the first side wall interior surface from sticking to the second side wall interior surface.

22 Claims, 1 Drawing Sheet

ADHERENT CELL CULTURE FLASK

This application is a continuation of application Ser. No. 264,595, filed Oct. 31, 1988, now abandoned.

BACKGROUND OF THE INVENTION

The present invention relates in general to flexible containers for containing a product. More specifically, the present invention relates to a cell culture flask for containing adherent cells.

It is known to grow cells in vitro by placing the cells in a cell culture media. A typical cell culture media includes a solution of amino acids, electrolytes, and vitamins.

There are two major types of cells grown in vitro: suspension cells (anchorage-independent cells); and adherent cells (anchorage-dependent cells). Suspension or anchorage-independent cells can multiply, in vitro, without being attached to a surface. In contrast, however, anchorage-dependent cells (hereinafter "adherent cells") require attachment to a surface in order to grow in vitro.

It is known to grow adherent cells, in vitro, in polystyrene flasks. Typically, the polystyrene flasks are treated by known means to produce a negative charged or positive charged inner surface. The adherent cells attach themselves to this charged active surface.

SUMMARY OF THE INVENTION

The present invention provides an improved container for containing adherent cells to be grown in vitro. To this end, the present invention provides a flexible adherent cell culture flask comprising a body constructed from a first side wall and a second side wall, each side wall having an interior surface and an exterior surface. The first and second side walls are sealed together to define an interior chamber. The first side wall is constructed from a flexible film and includes an interior surface, means for facilitating the attachment of cells thereto. The second side wall is constructed from flexible film and includes on an interior surface, means for preventing the first side wall interior surface from sticking to the second side wall interior surface.

Preferably, at least one of the first or second side walls is constructed from a gas permeable film.

Preferably, the interior surface of the first side wall is either negatively or positively charged depending on the cells to be grown in vitro and presents a smooth surface for cell growth and cell viewing.

Preferably, the interior surface of the second side wall does not adhere to the interior surface of the first side wall.

In an embodiment, the interior surface of the second side wall includes ribs projecting from a surface thereof.

In an embodiment of the present invention, the interior surface of the second side wall includes a taffeta or other matte surface or other non-smooth surface.

In an embodiment, the side walls are constructed from ethylene-vinyl acetate.

Preferably, the cell culture flask includes at least one access port for accessing the interior chamber of the flask.

An advantage of the present invention is that it provides an improved adherent cell culture container for growing adherent cells in vitro.

Moreover, an advantage of the present invention is that it provides an adherent cell culture container having at least one interior surface to which the cells can adhere.

A further advantage of the present invention is to provide a container having interior surfaces that are different, preventing a first interior surface from sticking to a second interior surface during manufacturing and sterilization of the container.

Still an advantage of the present invention is that it provides a container having sufficient gas permeability characteristics allowing gas exchange without venting the container, thus decreasing the risk of contamination or accidents with biohazardous agents.

Furthermore, an advantage of the present invention is that it provides a container that is more permeable to oxygen and carbon dioxide than typical conventional cell culture flasks.

Another advantage of the present invention is that it provides a cell culture container that is difficult to break.

A still further advantage of the present invention is that it provides a cell culture flask having increased handling characteristics such as: centrifugation; cryopreservation; and decreases labor costs.

An additional advantage of the present invention is that it provides a cell culture container that is sufficiently transparent so that the cell culture can be viewed.

Additional features and advantages of the present invention will be apparent from the detailed description of the presently preferred embodiments and from the drawings.

DETAILED DESCRIPTION OF THE PRESENTLY PREFERRED EMBODIMENTS

The present invention provides an improved adherent cell culture flask. As used herein, the term "adherent" refers to cells that must be anchored, or attached, to a surface in order to multiply in vitro.

Figure 1:
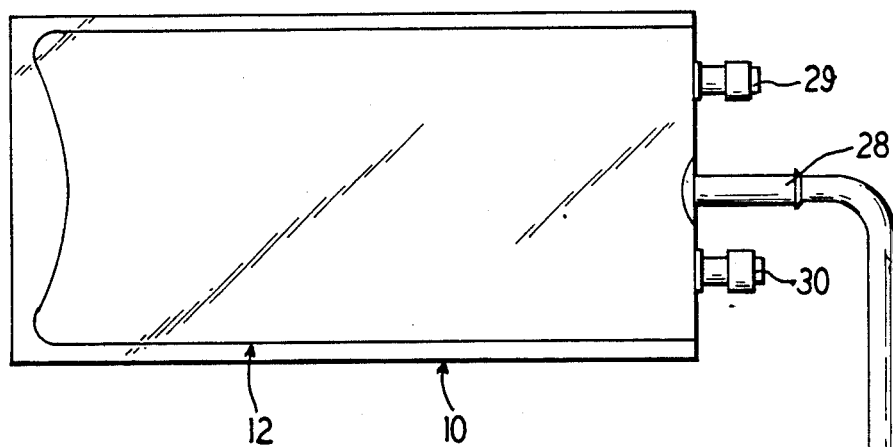
FIG. 1 illustrates a perspective view of an embodiment of the adherent cell culture flask of the present invention.
Figure 2:
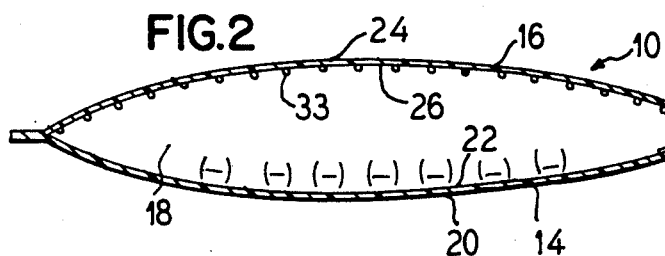
FIG. 2 illustrates a cross-sectional view of the adherent cell culture flask of FIG. 1 taken along lines II—II of FIG. 1.
Figure 3:
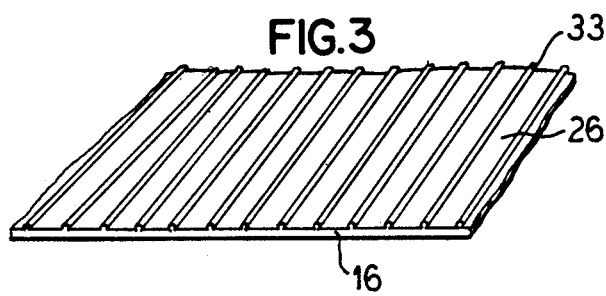
FIG. 3 illustrates a perspective view of a portion of the side wall of the container of FIG. 1.

FIGS. 1, 2, and 3 illustrate an embodiment of the adherent cell culture container 10 of the present invention. As illustrated, the container includes a body 12 that is constructed from a first side wall 14 and a second side wall 16. The side walls 14 and 16 are sealed along their edges to define a containment area 18 for housing a product.

The first side wall 14 includes an exterior surface 20 and an interior surface 22. Likewise, the second side wall 16 includes an exterior surface 24 and an interior surface 26. The exterior surfaces 20 and 24 define, at least in part, the outer surface of the body 12 of the container 10. The interior surfaces 22 and 26 define, at least in part, the containment area 18 of the container 10. As set forth in more detail below, the interior surface 22 of the first side wall 14 defines a cell growth surface.

In the embodiment of the container 10 illustrated, the container 10 includes access ports 28, 29, and 30. The access ports 28, 29, and 30 facilitate filling the container 10 with cells and/or cell culture media, and, the removal of same. Of course, any number of access ports can be provided as well as a tube set assembly, or the like.

The side walls 14 and 16 of the container 10 are constructed from flexible film. Preferably, the first side wall 14, whose interior surface 22 defines a cell growth surface, is constructed from a gas permeable flexible plastic film. The film preferably has good gas permeability, especially with respect to oxygen and carbon dioxide, allowing these gases to pass across the surface during the cell growth process. Preferably, the film is optically clear allowing cell growth on the interior surface 22 to be examined by a microscope or other means without having to access the cells contained therein.

To provide a cell growth surface, the interior surface 22 of the first side wall 14 is smooth and charged. Depending on the adherent cells to be grown in vitro, the interior surface 22 is either negatively or positively charged to facilitate attachment. Most adherent cells require a negatively charged surface to facilitate attachment. A small number of cells, however, require a positively charged surface. Preferably, the interior surface 22 has an energy of approximately 60 dyne/centimeter or greater. The film can be charged by known means such as irradiation by electron beam, corona or plasma discharge. In a preferred embodiment, the film is an ethylene-vinyl acetate.

The second side wall 16 is also preferably constructed from a gas permeable flexible plastic film. In a preferred embodiment, the plastic film is transparent or translucent. In contrast to the interior surface 22 of the first side wall 14, the interior surface 26 of the second side wall 16 includes a non-smooth or rough surface. To this end, the interior surface 26 of the second side wall 14 is matte, taffeta, or ribbed, for example. As used herein, the term "matte" means that the surface is rough or granular, non smooth.

In the embodiment of the container 10 illustrated in FIGS. 2 and 3, the interior surface 26 of the second side wall 16 includes a plurality of raised ribs 33.

Figure 4:
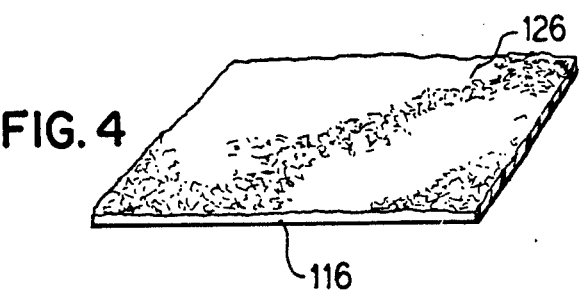
FIG. 4 illustrates a perspective view of a portion of a side wall of an embodiment of the adherent cell culture flask of the present invention.

FIG. 4 illustrates a portion of the interior surface of the second side wall of another embodiment of the container of the present invention. As illustrated, the interior surface 126 of the second side 116 is matte, i.e., has an uneven surface texture.

Because the interior surface 26 or 126 of the second side wall 16 or 116 is not smooth, e.g., ribbed or matte, the interior surface 22 of the first side wall 14, i.e., the growth surface, will not stick to the interior surface 26 or 126 of the second side wall 16 or 116. This is especially a concern during the process of manufacturing the container 10 and the sterilization of same. If the two interior surfaces 22 and 26 stick together it is difficult and time consuming to utilize the resultant container 10 as an adherent cell flask in that the surfaces must be pulled apart prior to any such use.

Although the interior surface 26 of the second side wall 16 has a different construction than the interior surface 22 of the first side wall 14, i.e., has a rougher surface, the second side wall 16 in an embodiment can also be constructed from ethylene-vinyl acetate. However, the second side wall 16 can be constructed from a different flexible material than the first side wall 14, such as, for example, any polyolefin.

In a preferred embodiment, the body 12 of the container 10 is constructed from a blown film. In an embodiment, preferably, the film from which the body 12 of the container 10 is made is heat sealable.

In use, a container 10 is constructed having either a positively or negatively charged interior surface 22, dependent on the cells to be grown in vitro. Due to the construction of the interior surfaces 22 and 26 of the first side wall 14 and second side wall 16, respectively, the side walls do not stick together.

Adherent cells to be grown in vitro and cell culture media are introduced into the containment area 18 of the container 10 through one or more of the ports 28, 29, or 30. The ports may then be sealed if desired. However, the ports can include an injection site or port tube and therefore are not sealed. In the embodiment of the present invention illustrated, port 28 includes a port tube.

Due to the charged interior surface 22, and the positioning of the container 10 such that the side wall with the charged surface, is lower than the noncharged surface, the cells will adhere to the charged interior surface and grow in vitro. If desired, both interior surfaces can be charged. Because the clarity of the film used to construct the first side wall 14, the cell growth on the interior surface 22 can, be examined by a microscope or other means. If desired, the cell culture can be accessed from the container through ports 29 and 30 or other materials can be added to the container 10 through the ports.

The walls of the container 10 can be constructed from any film composition that exhibits sufficient properties of clarity, gas permeability, and cell performance.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A gas permeable cell culture flask for growing adherent cells in vitro comprising a body constructed from a gas permeable flexible film, the body having a first interior surface and a second interior surface that define a containment area, the first interior surface having a charged surface for facilitating attachment of adherent cells to the first interior surface and the second interior surface having a non-smooth surface for preventing the first interior surface from sticking to the second interior surface during a process for manufacturing and sterilizing the flask.

2. The gas permeable cell culture flask of claim 1 wherein the first interior surface is negatively charged.

3. The gas permeable cell culture flask of claim 1 wherein the first interior surface is positively charged.

4. The gas permeable cell culture flask of claim 1 wherein the second interior surface has a matte texture.

5. The gas permeable cell culture flask of claim 1 wherein the second interior surface includes ribs.

6. The gas permeable cell culture flask of claim 1 wherein the body is constructed from ethylene-vinyl acetate.

7. The gas permeable cell culture flask of claim 1 wherein the flask includes at least one access port for accessing the containment area.

8. The gas permeable cell culture flask of claim 1 wherein the first interior surface has a surface energy of at least 60 dyne per centimeter.

9. A method of culturing a cell line comprising the steps of:
providing a container that defines a containment area;
providing the container with a first interior surface that is charged;
providing the container with a second interior surface, located diametric to the first interior surface, that has a non-smooth surface;
introducing a cell line into the containment area;
allowing the cell line to attach to the first interior surface; and
allowing gases, including oxygen and carbon dioxide, to permeate through at least one wall of the container.

10. The method of claim 9 including the step of providing the first interior surface with a negative charge.

11. The method of claim 9 including the step of providing the first interior surface with a positive charge.

12. The method of claim 9 including the step of providing the first interior surface with a surface of energy of at least 40 dyne per centimeter.

13. The method of claim 9 including the step of constructing the first interior surface so that it is smooth and optically clear.

14. An adherent cell culture flask comprising a body constructed from a first side wall and a second side wall, each side wall having an interior surface and an exterior surface, the first and second side walls being sealed to define a chamber, the first side wall being constructed from flexible film and including on its interior surface means for facilitating the attachment of cells thereto, wherein the interior surface of the first side wall is negatively charged, the second side wall being constructed from flexible film and including on its interior surface means for preventing the first side wall interior surface from sticking to the second side wall interior surface.

15. An adherent cell culture flask comprising a body constructed from a first side wall and a second side wall, each side wall having an interior surface and an exterior surface, the first and second side walls being sealed to define a chamber, the first side wall being constructed from flexible film and including on its interior surface means for facilitating the attachment of cells thereto, wherein the interior surface of the first side wall is positively charged, the second side wall being constructed from flexible film and including on its interior surface means for preventing the first side wall interior surface from sticking to the second side wall interior surface.

16. An adherent cell culture flask comprising a body constructed from a first side wall and a second side wall, each side wall having an interior surface and an exterior surface, the first and second side walls being sealed to define a chamber, the first side wall being constructed from flexible film and including on its interior surface means for facilitating the attachment of cells thereto, the second side wall being constructed from flexible film and including on its interior surface means for preventing the first side wall interior surface from sticking to the second side wall interior surface, said means including ribs projecting from a surface of said second sidewall.

17. An adherent cell culture flask comprising a body constructed from a first side wall and a second side wall, each side wall having an interior surface and an exterior surface, the first and second side walls being sealed to define a chamber, the first side wall being constructed from flexible film and including on its interior surface means for facilitating the attachment of cells thereto, the second side wall being constructed from flexible film, wherein the interior surfaces of both the first and second side walls are charged, said second side wall further including on its interior surface means for preventing the first side wall interior surface from sticking to the second side wall interior surface.

18. The adherent cell culture flask of claim 14, 15, 16 or 17 wherein at least one of the first and second side walls is constructed from a gas permeable film.

19. The adherent cell culture flask of claim 14, 15, 16 or 17 wherein the interior surface of the second side wall is not smooth.

20. The adherent cell culture flask of claim 14, 15, 16 or 17 including an access port for accessing the chamber.

21. The adherent cell culture flask of claim 14, 15, 16 or 17 wherein at least one of the first or second side walls is constructed from ethylene-vinyl acetate.

22. The adherent cell culture flask of claim 14, 15, 16 or 17 wherein the interior surface of the first side wall is optically clear and smooth.

* * * * *